(12) United States Patent
Clark et al.

(10) Patent No.: US 9,247,955 B2
(45) Date of Patent: Feb. 2, 2016

(54) THORACIC ACCESS PORT

(75) Inventors: Charlotte Adele Clark, Cambridge (GB); Thomas John Hector Copeland, Cambridge (GB); Cormac O'Prey, Bishops Stortford (GB); Rebecca Ann Wilkins, Royston (GB); Daniel Leonard Fuller, Haverhill (GB)

(73) Assignee: Covidien LP, Mansfield, MA (US)

( * ) Notice: Subject to any disclaimer, the term of this patent is extended or adjusted under 35 U.S.C. 154(b) by 952 days.

(21) Appl. No.: 13/166,875

(22) Filed: Jun. 23, 2011

(65) Prior Publication Data

US 2012/0041335 A1 Feb. 16, 2012

Related U.S. Application Data

(60) Provisional application No. 61/372,960, filed on Aug. 12, 2010.

(51) Int. Cl.
*A61B 1/32* (2006.01)
*A61B 17/34* (2006.01)
*A61B 17/02* (2006.01)

(52) U.S. Cl.
CPC ......... *A61B 17/3423* (2013.01); *A61B 17/0218* (2013.01); *A61B 17/3431* (2013.01); *A61B 17/3439* (2013.01); *A61B 2017/0225* (2013.01); *A61B 2017/3427* (2013.01); *A61B 2017/3482* (2013.01); *A61B 2017/3488* (2013.01)

(58) Field of Classification Search
CPC .............. A61B 17/02; A61B 17/0218; A61B 2017/0225; A61B 17/0281; A61B 2017/0287; A61B 1/32; A61B 17/3423; A61B 2017/3427

USPC .................................. 600/231–233, 206, 208
See application file for complete search history.

(56) References Cited

U.S. PATENT DOCUMENTS

| 1,780,912 | A |   | 11/1930 | Gau |
| 1,810,466 | A |   | 6/1931  | Deutsch |
| 2,313,164 | A | * | 3/1943  | Nelson .......................... 600/208 |

(Continued)

FOREIGN PATENT DOCUMENTS

| DE | 10001695 | 2/2001 |
| DE | 102009014527 | 9/2010 |

(Continued)

OTHER PUBLICATIONS

EP Search Report 11 25 0163 dated Jun. 7, 2011.

(Continued)

*Primary Examiner* — Todd E Manahan
*Assistant Examiner* — Julianna N Harvey (57) ABSTRACT

A surgical access port for accessing a cavity of a patient having an outer frame including first and second frame portions, wherein at least one of the frame portions is movable with respect to the other frame portion. The outer frame has a first length greater than the first width, wherein movement of at least one of the frame portions away from the other frame portion increases the outer frame to a third length greater than the first length. An inner member has a second length and a second width, the second length being substantially transverse to the first length of the outer frame and the second width being substantially transverse to the first width of the outer frame. A flexible member extends between the outer frame and inner member and is movable by movement of at least one of the frame portions.

17 Claims, 9 Drawing Sheets

(56) References Cited

U.S. PATENT DOCUMENTS

| | | |
|---|---|---|
| 2,541,516 A | 2/1951 | Ivory et al. |
| 2,812,758 A | 11/1957 | Blumenschein |
| 3,782,370 A | 1/1974 | McDonald |
| 3,807,393 A | 4/1974 | McDonald |
| 3,965,890 A | 6/1976 | Gauthier |
| 4,130,113 A | 12/1978 | Graham |
| 4,263,899 A | 4/1981 | Burgin |
| 4,553,537 A | 11/1985 | Rosenberg |
| 5,007,900 A | 4/1991 | Picha et al. |
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Cook |
| 5,556,385 A | 9/1996 | Andersen |
| 5,562,677 A | 10/1996 | Hildwein et al. |
| 5,653,705 A | 8/1997 | De la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | De la Torre et al. |
| 6,033,362 A | 3/2000 | Cohn |
| 6,033,425 A | 3/2000 | Looney et al. |
| 6,033,426 A | 3/2000 | Kaji |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 * | 7/2001 | Fadem et al. ................. 600/208 |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | De la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1 | 3/2004 | Ewers et al. |
| 2004/0054353 A1 * | 3/2004 | Taylor .............................. 606/1 |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0030861 A1 * | 2/2006 | Simonson et al. .............. 606/99 |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0073110 A1 | 3/2007 | Larson et al. |
| 2007/0167980 A1 | 7/2007 | Figulla |
| 2007/0225569 A1 * | 9/2007 | Ewers et al. .................. 600/206 |

(56) References Cited

U.S. PATENT DOCUMENTS

| | | |
|---|---|---|
| 2008/0132766 A1 | 6/2008 | Dant et al. |
| 2008/0234550 A1 | 9/2008 | Hawkes et al. |
| 2009/0105655 A1 | 4/2009 | Desantis |
| 2009/0204067 A1 | 8/2009 | Abu-Halawa |
| 2009/0265941 A1 | 10/2009 | Kurrus |
| 2009/0299148 A1 | 12/2009 | White et al. |
| 2009/0326469 A1 | 12/2009 | Rockrohr |
| 2010/0168522 A1 | 7/2010 | Wenchell |
| 2010/0210916 A1 | 8/2010 | Hu et al. |
| 2010/0234689 A1 | 9/2010 | Wagner et al. |
| 2010/0261970 A1 | 10/2010 | Shelton, IV et al. |
| 2010/0298646 A1 | 11/2010 | Stellon |
| 2011/0021879 A1 | 1/2011 | Hart et al. |

FOREIGN PATENT DOCUMENTS

| | | |
|---|---|---|
| EP | 0177177 | 4/1986 |
| EP | 2179699 | 4/2010 |
| EP | 2179699 A1 | 4/2010 |
| EP | 2 228 014 | 9/2010 |
| EP | 2 228 024 | 9/2010 |
| EP | 2 238 931 A1 | 10/2010 |
| EP | 2 422 725 | 2/2012 |
| EP | 2417922 | 2/2012 |
| EP | 2417922 A1 | 2/2012 |
| EP | 2 462 883 | 6/2012 |
| GB | 2275420 | 8/1994 |
| JP | 2003-199748 A | 7/2003 |
| JP | 2006-320750 A | 11/2006 |
| WO | WO95/00197 | 1/1995 |
| WO | WO95/15715 | 6/1995 |
| WO | WO 01/08563 A2 | 2/2001 |
| WO | 03/034908 A2 | 5/2003 |
| WO | WO-03/034908 | 5/2003 |
| WO | 2005/089655 A1 | 9/2005 |
| WO | WO-2005/089655 | 9/2005 |
| WO | WO2010/042913 | 4/2010 |
| WO | WO 2010/136805 | 12/2010 |
| WO | WO 2011/079374 | 7/2011 |

OTHER PUBLICATIONS

EP Search Report 11 25 0164 dated Jun. 8, 2011.
EP Search Report Ep 12 15 4733 dated Jan. 14, 2014.
EP Search Report EP 11 19 1403 dated Dec. 11, 2013.
EP Search Report EP 12160423.5 dated Jun. 25, 2012.
EP Search Report EP 11 18 9987 dated Feb. 15, 2012.
European Search Report EP 12180474 dated Nov. 20, 2012.
Partial European Search Report EP 12168483 dated Nov. 9, 2012.
Japanese Office Action for Japanese Appln. No. 2011-167059 mailed Apr. 28, 2015.

* cited by examiner

THORACIC ACCESS PORT

This application claims priority from provisional application Ser. No. 61/372,960, filed Aug. 12, 2010, the entire contents of which are incorporated herein by reference.

BACKGROUND

1. Technical Field

The present disclosure relates generally to devices and techniques for performing surgical procedures. More particularly, the present disclosure relates to an expandable access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's sometimes body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments are inserted into the internal work site through the passageway in the access assembly.

In the interests of facilitating visualization, the introduction of certain surgical instruments, and/or the removal of tissue specimens during minimally invasive thoracic procedures, it may be desirable to spread/retract the tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for a thoracic access port which minimizes post operative patient pain while enabling atraumatic retraction of tissue and which do not restrict access to the body cavity, as well as facilitates removal of tissue specimens from the body cavity.

SUMMARY

The present application provides in one aspect a surgical access port for accessing a cavity of a patient comprising an outer frame having first and second frame portions, at least one of the frame portions movable with respect to the other frame portion. The outer frame has a first length defined along a longitudinal axis and a first width, the first length being greater than the first width, wherein movement of at least one of the frame portions away from the other frame portion increases the outer frame to a third length greater than the first length. An inner member has a second length defined along a longitudinal axis and a second width, the second length being greater than the second width. The second length of the inner member is substantially transverse to the first length of the outer frame and the second width of the inner member is substantially transverse to the first width of the outer frame. A flexible member extends between the outer frame and inner member, the flexible member movable by movement of at least one of the frame portions.

In one embodiment, the first frame portion has a first end wall and first and second side walls wherein at least one of the first and second side walls has an opening formed therein, and the second frame portion has a second end wall and third and fourth side walls extending from the second end wall, at least one of the third and fourth side walls terminating in a substantially linear portion insertable into the opening. In some embodiments, each of the first and second side walls terminate in an opening and each of the third and fourth side walls terminate in a substantially linear portion insertable into the respective openings of the first and second side walls.

The first and second side walls can include a tapered portion. The outer frame and inner member preferably include a flexible member mounting surface.

In some embodiments, the inner member includes a lip extending toward the outer frame and substantially surrounding a lower access opening in the inner member.

In preferred embodiments, the outer frame and inner member are substantially rectangular in configuration. Other shapes are also contemplated.

The flexible member can have a funnel shape narrowing in a direction toward the inner member. In some embodiments, movement of at least one of the frame portions increases the length of the outer frame to stretch the membrane in a direction away from longitudinal edges of an elongated access incision in the patient.

In some embodiments, the first length of the outer frame is greater than the second length of the inner member and the first width of the outer frame is greater than a second width of the inner member. In some embodiments, the second length of the inner member does not exceed the first width of the outer frame.

The present disclosure provides in another aspect a surgical access port for accessing a cavity of a patient comprising an outer frame having first and second frame portions, at least one of the frame portions movable with respect to the other frame portion. The outer frame has a first length defined along a longitudinal axis, wherein movement of at least one of the frame portions away from the other frame portion increases the outer frame to a third length greater than the first length. An inner member has an access opening and a lip adjacent the opening, the lip extending proximally toward the outer frame for positioning in an access incision of the patient. A flexible member extends between the outer frame and inner member, the flexible member movable by movement of at least one of the frame portions.

In some embodiments, movement of at least one of the frame portions increases the length of the outer frame to stretch the membrane in a direction away from longitudinal edges of an elongated access incision in the patient. In some embodiments, the access opening has a length greater than a width and the lip extends substantially around a perimeter of the access opening.

In another aspect, a method of inserting a surgical access port into a thoracic cavity is provided comprising the steps of:

providing an access port having an outer frame, an inner member with a proximally extending lip, and a flexible member extending between the inner member and outer frame;

reconfiguring the inner member for insertion through an incision of the patient;

inserting the inner member through the incision and enabling the inner member to return to a placement position such that the inner member is positioned in the cavity and the flexible member extends through the incision and such that the inner member is oriented so that a longitudinal axis is substantially aligned with a long axis of the incision and the lip extends into a portion of the incision; and expanding the outer frame by moving at least a first portion of the outer frame in a direction of movement transverse to the long axis of the incision thereby tensioning the flexible member to retract tissue adjacent the incision.

The method may further comprise the steps of inserting a surgical instrument thought the access port and withdrawing a tissue specimen through the access port. The method may also include the step of reconfiguring the inner member to remove it from the cavity of the patient and out of the incision.

DESCRIPTION OF THE DRAWINGS

Various embodiments of the subject access port are disclosed herein with reference to the drawings, wherein.

DETAILED DESCRIPTION OF EMBODIMENTS

Embodiments of the presently disclosed surgical access port will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

The surgical access port disclosed herein is described for use as a thoracic access port to provide access to the thoracic cavity. It should also be understood that the access port can be utilized for access to other parts, e.g. cavities, of the patient in other minimally invasive procedures.

Figure 1:
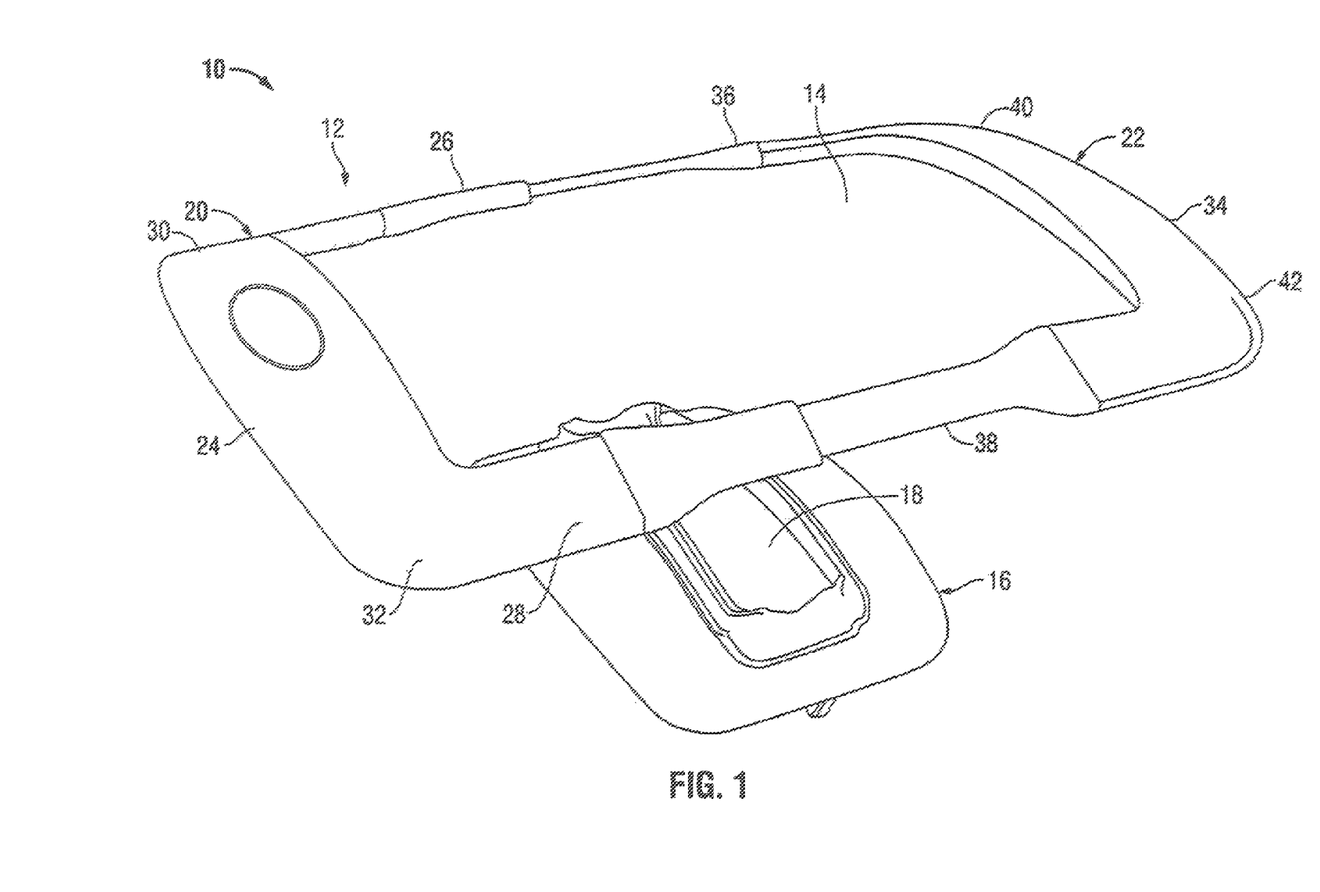
FIG. 1 is a top perspective of an adjustable surgical access port of the present disclosure shown in a spread position (the flexible member removed for clarity)
Figure 8:
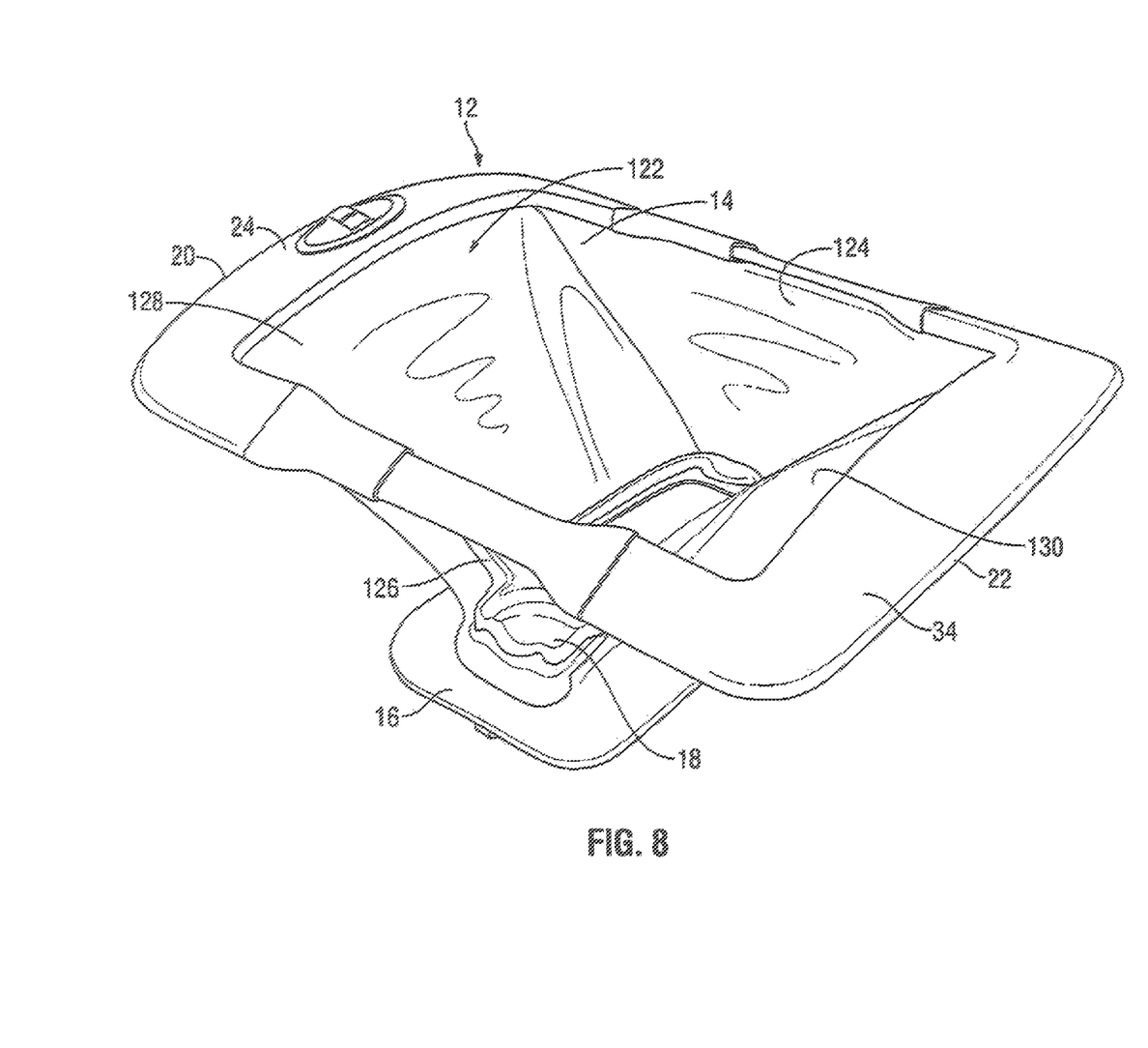
FIG. 8 is a perspective view of the access port of FIG. 1 with the flexible member attached.

Referring initially to FIGS. 1 and 8, access port 10 includes a proximal or upper body member or frame 12 defining an upper access opening 14 and a distal or lower body member or frame 16 defining a lower access opening 18. Upper access opening 14 and lower access opening 18 provide an access pathway for receipt of surgical instrumentation therethrough to access the body cavity of a patient. Flexible member 130 extends between frames 12 and 16 and is tensioned or stretched by movement of the frame 12 as described below. The flexible member 130 is not shown in FIG. 1 for clarity; it is illustrated in FIG. 8. In use as described below, proximal member 12 is positioned outside the patient's body, thus constituting an "outer" member and distal member 16 is positioned inside the patient, thus constituting an "inner" member.

Upper (outer) frame 12 includes a first U-shaped member or frame portion 20 and a second U-shaped member or frame portion 22, facing one another. Together the two members (portions) 22, 24 form a substantially rectangular upper frame 12. Other shapes are also contemplated. First member 20 and second member 22 can be formed of relatively rigid materials and are movably interconnected so as to adjust the size of upper access opening 14 and adjust the tension of flexible member 130 against tissue as discussed in more detail below. The members 20 and 22 can also be formed of semi-rigid or flexible materials.

Figure 2:
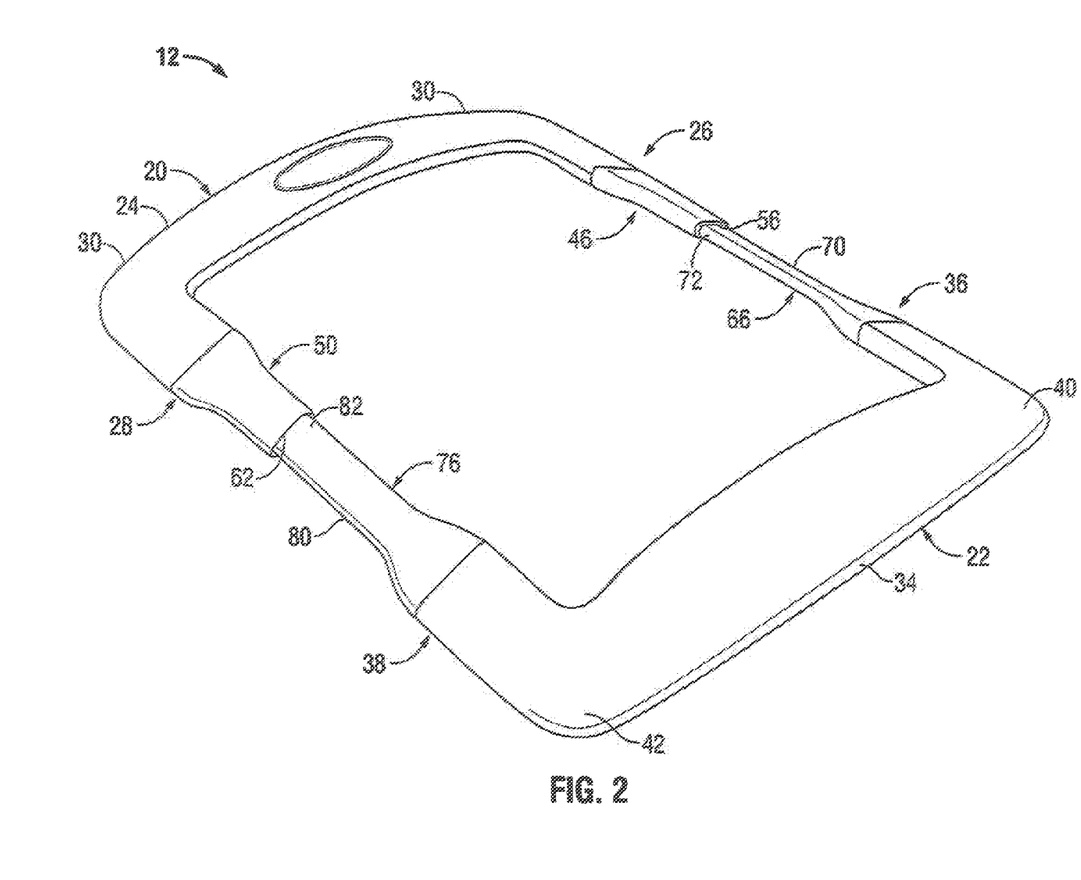
FIG. 2 is a top perspective view of the outer member (frame)
Figure 3:
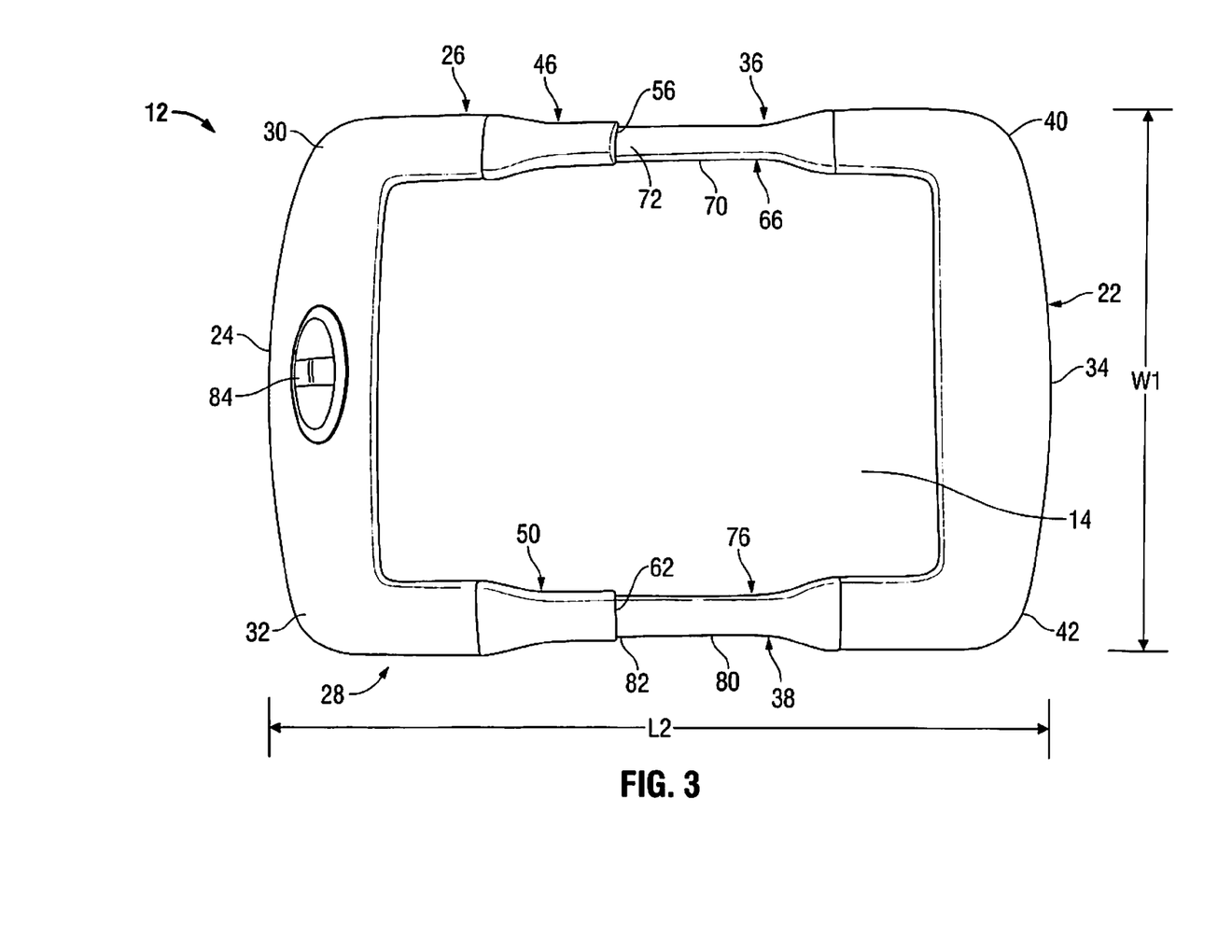
FIG. 3 is a top plan view of the outer member in an expanded condition.

First member 20 includes a first end wall 24 having first and second side walls 26, 28 extending from respective first and second opposed ends 30 and 32 of wall 24 (see also FIGS. 2 and 3). Similarly, second member 22 includes a second end wall 34 having third and fourth side walls 36, 38 extending from respective first and second opposed ends 40 and 42 of second end wall 34.

First side wall 26 includes a tapered portion 46, narrowing in width in a direction away from end wall 24, and terminating in an opening 56. Similarly, second side wall 28 includes a second tapered portion 50, narrowing in width in a direction away from end wall 24, and terminating in an opening 62.

Third side wall 36 of second member 22 includes a third tapered portion 66, narrowing in width in a direction away from end wall 34, and tapering to a substantially linear portion 70 which terminates in an insertion end 72. Insertion end 72, along with substantially linear portion 70, is sized to be received within opening 56 of first tapered portion 46. In the illustrated embodiment, it is frictionally received within opening 56.

Fourth side wall 38 includes a fourth tapered portion 76, narrowing in width in a direction away from end wall 34, and tapering to a substantially linear portion 80 which terminates in an insertion end 82. Insertion end 82, along with substantially linear portion 80, is sized to be received within opening 62 in second tapered portion 50. In the illustrated embodiment, it is frictionally received within opening 56.

It should be noted that while the interconnections between linear portions 70 and 80 within openings 56 and 62 are described as being frictional, other methods of releasably securing them may be provided.

Upper frame 12 is adjustable between contracted (non-expanded) and expanded (spread) conditions. To facilitate adjusting upper frame 12, a finger tab 84 (FIG. 3) can optionally be provided. The surgeon may alternatively or additionally grasp wall 24 and/or 34 and pull them away from each other or with his/her thumb, moving the walls 24 and/or 34 in opposite directions. Thus, adjustment is achieved by relative movement of the U-shaped members (portions) 20, 22, such relative movement including movement of member 20 while member 22 is held stationary, movement of member 22 as member 20 is held stationary, or movement of both members 20, 22 away from each other.

Figure 4:
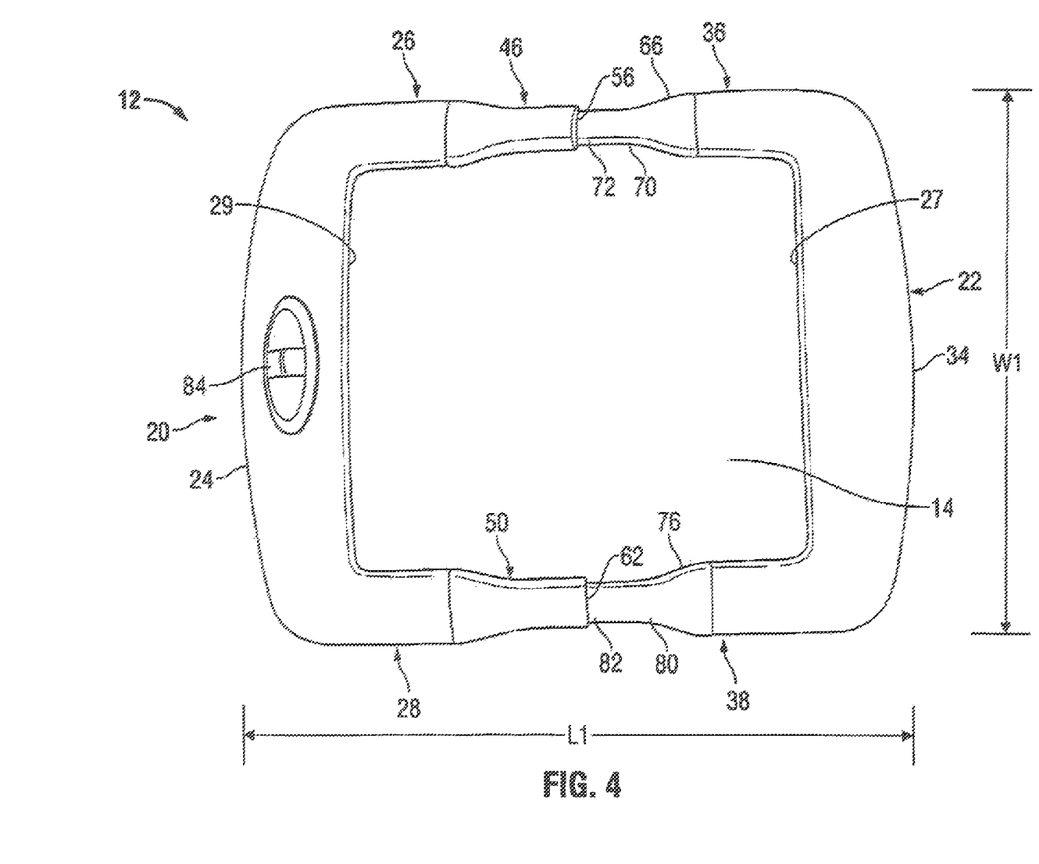
FIG. 4 is a top plan view of the outer member in a contracted (non-expanded) condition.

In the contracted position of FIG. 4, which is preferably the initial position of the access port 10, walls 24 and 34 are closer together than in the expanded (spread) position of FIG. 3.

That is, in the contracted position, the distance between the walls 24 and 34 is less than the distance in the expanded position of FIG. 3. In the expanded condition, linear portions 70 and 80 of third and fourth tapered portions 66 and 76, respectively, are slidably received in openings 56 and 62 in first and second tapered portions 46 and 50 to a shallower extent.

In order to adjust outer frame 12 to an expanded position to tension the flexible member 130 described below, one or both of first and second walls 24 and 34 of first and second members 20 and 22 are slid away from each other so as to move linear portions 70 and 80 of third and fourth tapered portions 66 and 76 further away from first and second tapered portions 46 and 50 and further out of openings 56, 62.

In the contracted condition (FIG. 4), frame 12 has a first length L1 which is less than that of length L2 (FIG. 3) of the frame 12 in the expanded condition. The length of the access opening 14, defined as the distance between first and second inner edges 27, 29 of walls 24, 34, respectively, likewise is less in the contracted position of frame 12.

The length of the upper access opening 14 preferably exceeds its width, at least in the expanded position of the outer frame 12.

Also note that the outer frame 12 defines a width W1. Width W1 remains the same in the contracted and expanded positions. The width of the access opening 14 also remains the same in the contracted and expanded positions of outer frame 12. It should also be appreciated that preferably the length of the outer frame 12, at least in its expanded position, is greater than its width W1. The length can in some embodiments also be greater than the width W1 of the frame 12 in the contracted position.

As discussed hereinbelow, the ability to move first and second members 20 and 22 toward and away from each other allows first and second members 20 and 22 to stretch a flexible member 130, preferably in the form of a flexible membrane, affixed thereto in order to bring member 130 into tighter contact with tissue to retract the tissue surrounding the ribs. The flexible member 130 thus functions to protect the incision from contamination and to retract the tissue. Its shape also aids the guiding of a tissue specimen through the incision to facilitate removal from the body cavity.

Figure 5:
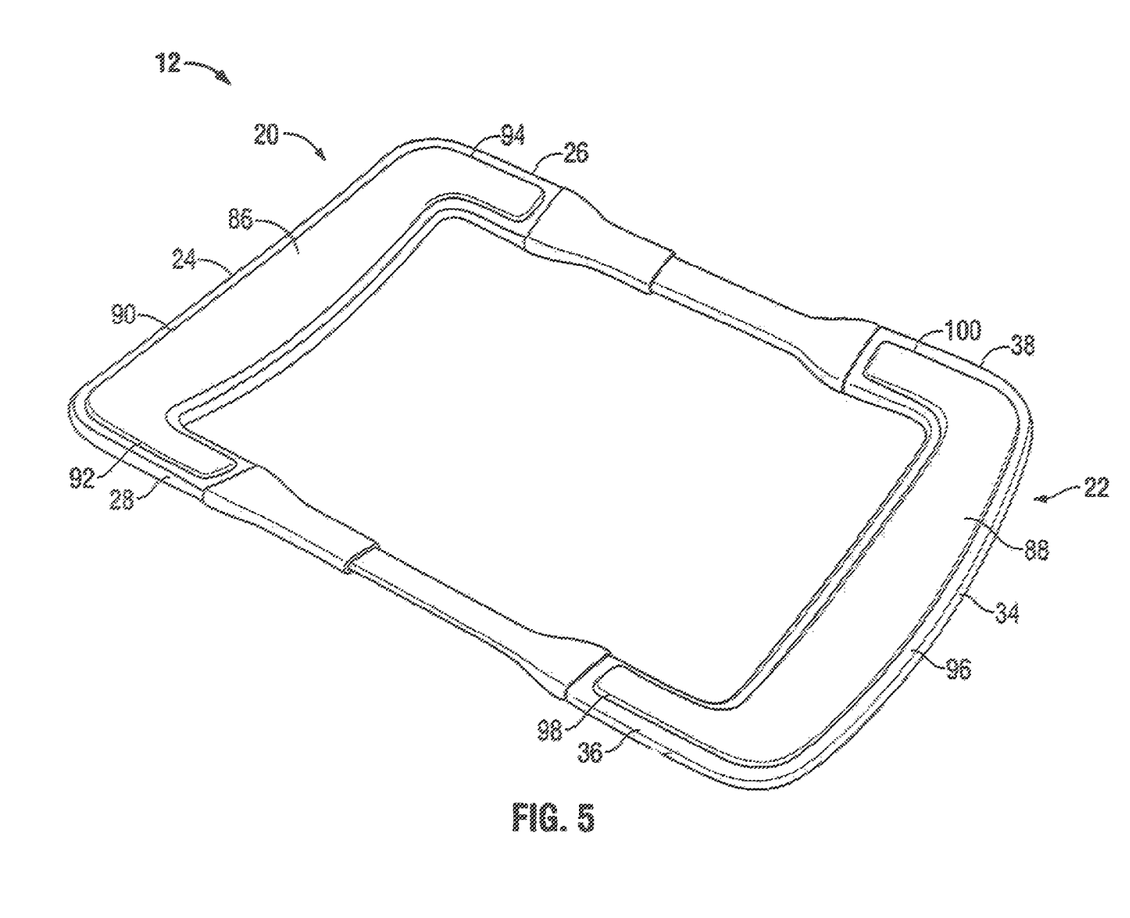
FIG. 5 is bottom perspective view of the outer member in the expanded condition.

In order to affix the flexible member such as membrane 130 to outer frame 12, outer frame 12 is provided with first and second membrane mounting surfaces 86 and 88 (FIG. 5). As shown, first membrane mounting surface 86 extends along an underside 90 of wall 24 as well as extending along under sides 92 and 94 of side walls 26, 28. Likewise, second membrane mounting surface 88 extends along an underside 96 of second wall 34 as well as extending along undersides 98 and 100 of side walls 36, 38. The membrane 130 (shown in FIG. 8) can be affixed to membrane mounting surfaces 86 and 88 through a variety of known methods such as adhesives, hot gluing, welding, etc.

Figure 6:
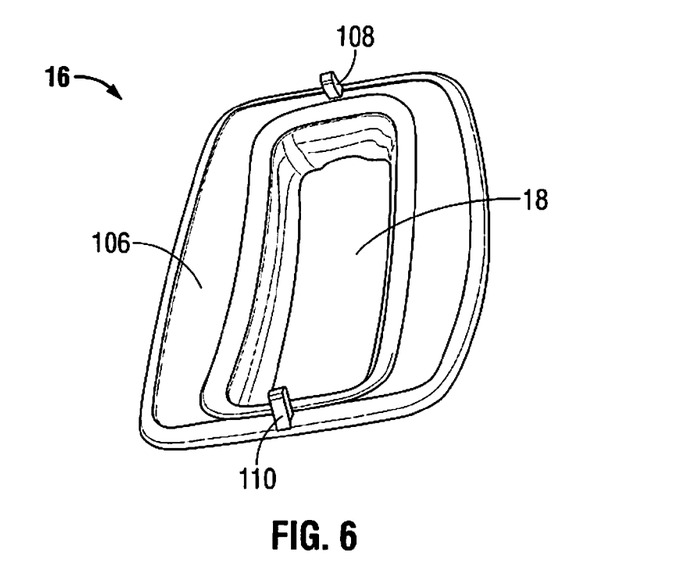
FIG. 6 is a bottom perspective view of the inner (lower) member.
Figure 7:
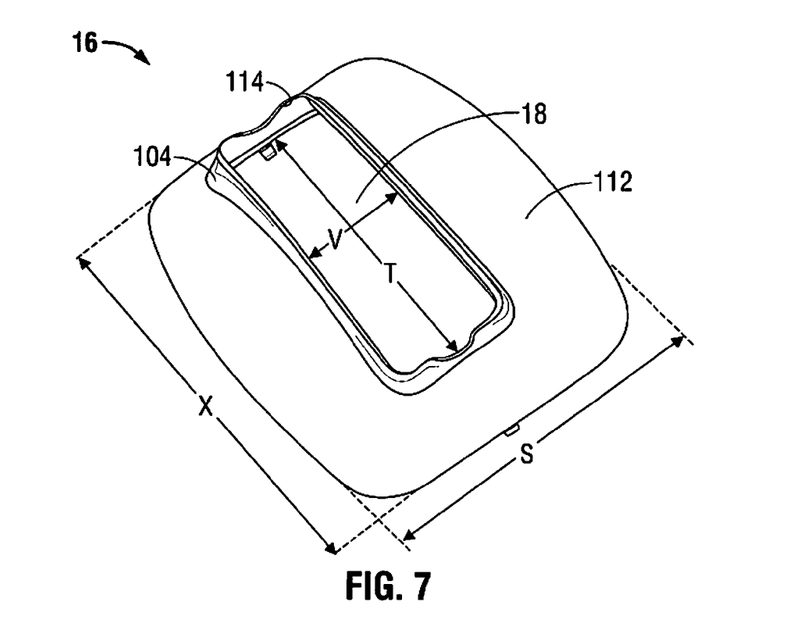
FIG. 7 is a top perspective view of the inner member.

Turning now to lower (proximal) or inner member or frame 16, and with reference to FIGS. 6 and 7, inner member 16 is preferably sufficiently flexible to be forced to a bent or reconfigured position for insertion through an incision. Member 16 is preferably substantially rectangular in configuration and has a length X defined along its longitudinal axis and a smaller width S transverse to the longitudinal axis. In the preferred embodiment, the length L1 (and L2) of the outer frame 12 is greater than the length X of inner member 16 and the width W1 of the outer member 12 is greater than the width S of the inner member 16. Note the length L1 of outer frame 12 is positioned substantially transverse to length X of inner member 16 and the width W1 of outer frame 12 is positioned substantially transverse to the width S of inner member 16. Thus, preferably length L1 can be substantially parallel to width S and width W1 can be substantially parallel to length X. In some embodiments, length X of inner member 16 does not exceed the width W1 of the outer member 12, and in some embodiments they are substantially equal. Note in one embodiment the relationship between the longitudinal axes of the outer member 12 and inner member 16 could be about 90 degrees.

Inner member 16 includes a lower access opening 18, having a length T defined along the longitudinal axis of the member 16 which is greater than the width V of the opening 18. A rib or lip 104, extending proximally toward the outer frame 12, substantially surrounds lower access opening 18, and preferably surrounds the entire opening, extending along the periphery. The proximalmost edge of lip 104 is designated by reference numeral 114. The lip 104 as shown is positioned inwardly of the outer edge of the lower member 16. The lip 104 is configured to extend into part of the incision and protect the nerves adjacent the ribs when the inner member 16 is positioned in the thoracic cavity of the patient. It can protect other tissue structure when used in other surgical applications. A membrane mounting surface 106 is provided on a top (proximal) surface of inner (lower) member 16 for mounting membrane 130 in a variety of known methods such as adhesives, hot gluing, welding, etc. Alternatively, the membrane 130 can be mounted to lip 104 by the foregoing methods. Note by attachment of the flexible member 130 at a proximal end to larger dimensioned outer frame 16 and at its distal end to smaller dimensioned inner frame 16, the flexible member 130 forms a funnel shape, narrowing in a distal direction.

Tabs 108 and 110 may be provided on inner body member 16 for receipt of sutures or to provide grasping surfaces for surgical instrumentation in order to facilitate insertion of removal of flexible inner member 16 from a patient. That is, one or both of the tabs 108, 110 can be grasped and pulled, thereby bending the inner member 16 to facilitate insertion and removal through the incision in the patient.

Flexible member 130 can be formed of a variety of known flexible, biocompatible materials and may additionally be transparent to better allow the surgeon to view the operative site. Flexible member 130 can be formed as a unitary component. Alternatively, it may be made of several separate components affixed to one another. For example, flexible member 130 may include first and second side panels 124 and 126 along with first and second end panels 128 and 130, or alternatively, and preferably, include two panels attached, e.g. welded, together to facilitate manufacture and reduce the number of seams. As adjustable outer frame 12 is expanded, flexible member 130 is tensioned to retract tissue as described below.

Figure 9:
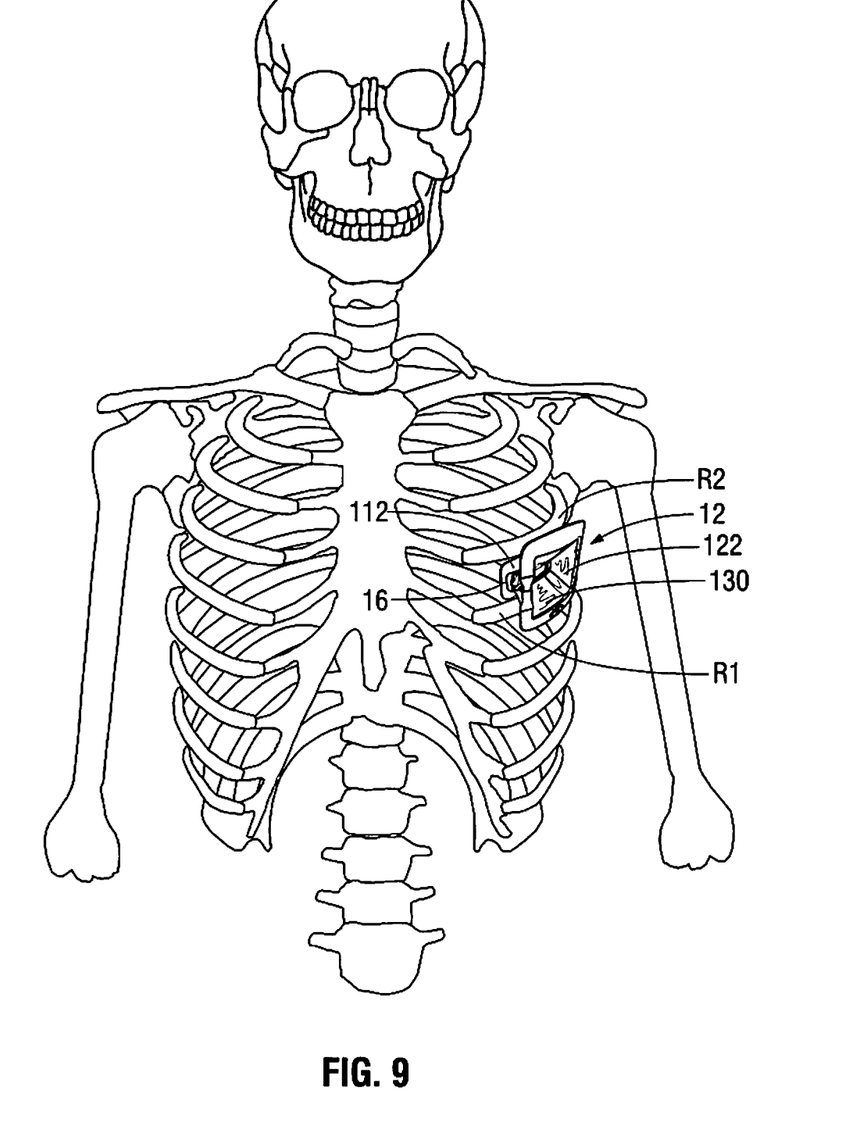
FIG. 9 is a perspective view illustrating the patient's skeletal structure with the outer member of the access port in the contracted condition positioned within the intercostal space defined between adjacent ribs.
Figure 10:
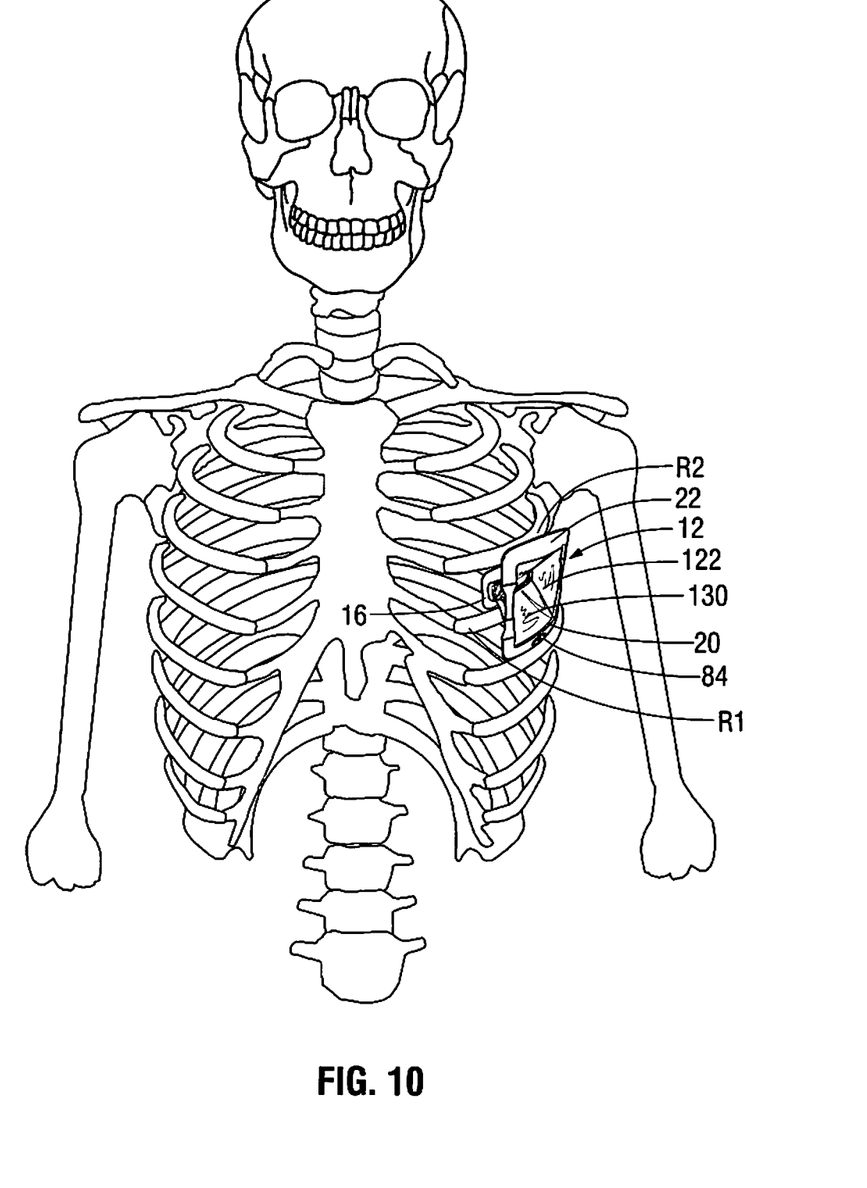
FIG. 10 is a perspective view similar to FIG. 9 showing the outer member in the expanded condition to tension the flexible member.

Use of thoracic access port 10 will now be described. An incision is made through the body tissue of a patient between adjacent ribs such as, for example, ribs R1 and R2 (FIGS. 9 and 10). Thereafter, flexible inner body member 16 of thoracic access port 10 is compressed or reconfigured, e.g. bent, using appropriate surgical instrumentation or by the surgeon's hands, and inserted between adjacent ribs R1 and R2. Once positioned within the thoracic cavity, inner member 16 is released to return to its original condition and is maneuvered to bring engaging surface 112 into engagement with tissue underlying ribs R1 and R2 and bring lip 104 extending into the incision. This may be facilitated by grasping outer frame 12 and pulling outer frame 12 in an upward direction. It should be noted that in this initial position, outer frame 12 is in the contracted condition (see FIG. 9). Flexible membrane 130 extends through and out from the incision, thereby protecting the incision from contamination. It should also be appreciated that in this placement position the longitudinal axis (along length X) of inner member 16 is positioned substantially along the length of the incision. This facilitates retraction of the tissue adjacent the incision since the incisions in thoracic surgery are generally elongated between the ribs. That is, in this manner, the access opening through the access port 10 better tracks the incision shape and therefore better accommodates the insertion and removal of instrumentation, and in particular better accommodates the insertion and removal of a tissue specimen.

Once inner member 16 has been properly positioned, upper frame 12 can be moved to the expanded position by grasping first and/or second end walls 24 and 34 and pulling them away from each other (see FIG. 10) to bring flexible member 130 into the desired tension against the incision and tissue adjacent ribs R1 and R2 in order to retract tissue (and to obtain the desired length of upper access opening 14). Note that outer frame 12 is positioned so that its longitudinal axis (along length L1 or L2) is substantially transverse to the longitudinal axis of the incision (and substantially transverse to the longitudinal axis of inner member 16). In this manner, the flexible member 130 is tensioned to widen the incision transverse to its long axis and the access opening is maximized.

Once the outer frame 12 is moved to a desired expanded position, a surgical procedure can be performed through thoracic access port 10 by inserting instrumentation and withdrawing tissue specimens through the access opening 14 in outer frame 12, the passageway 122 in the funnel shaped flexible member 130, and through lower access opening 18 in inner member 16. Note the funnel shaped flexible member 130, formed by its attachment at a proximal end to the larger dimensioned outer member 12 and at its distal end to smaller dimensioned inner member 16, facilitates removal of tissue specimens from the cavity. Once the procedure has been completed, outer frame 12 is returned to a contracted position to untension member 130 and then inner member 16 may be bent or reconfigured and withdrawn through the patient's incision. As noted above, tabs 108 and 110 on inner member 16 can facilitate removal of inner member 16 from the body of a patient as the inner member 16 is bent or reconfigured to reduce its transverse dimension.

As will be appreciated, access port 10 is easily inserted, manipulated, and removed from a patient's body. Further, the access port 10 is minimally intrusive, flexible to conform to a patient's anatomy, and provides good visibility into the thoracic cavity. Additionally, the low-profile configuration of access port 10 is particularly advantageous, for example, in the removal, or retrieval, of tissue specimens from within the body.

The flexible member 130 may be coated with a lubricant, or gel, to aid in the insertion and removal of surgical instrumentation and/or tissue specimens from access port 10.

Although described for use in thoracic procedures, it should also be understood that the access ports described herein can be used in other minimally invasive surgical procedures.

It will be understood that various modifications may be made to the embodiments disclosed herein. For example, either of the upper frame or inner member may be formed of a transparent material. Additionally, while disclosed as being generally rectangular, the frames and body members disclosed herein may include other shapes. Therefore, the above description should not be construed as limiting, but merely as exemplifications of particular embodiments. Those skilled in the art will envision other modifications within the scope and spirit of the claims appended hereto.

What is claimed is:

1. A surgical access port for accessing a cavity of a patient comprising:
   an outer frame having first and second frame portions defining a first access opening, at least one of the first or second frame portions movable with respect to the other one of the first or second frame portions, the outer frame having a first length along a first major axis thereof and a first width along a first minor axis thereof, the first length being greater than the first width, wherein movement of the at least one of the first or second frame portions away from the other one of the first or second frame portions increases the length of the outer frame to a third length greater than the first length;
   an inner member defining a second access opening, the inner member having a non-circular configuration, the inner member having a second length along a second major axis thereof and a second width along a second minor axis thereof, the second length being greater than the second width, the second length transverse to the second width, the inner member including a lip surrounding the second access opening, the entire lip positioned inwardly of an outer edge of the inner member; and
   a flexible member extending between the outer frame and the inner member, the flexible member movable by movement of the at least one of the first or second frame portions, wherein the second length of the inner member is substantially transverse to the first length of the outer frame when the flexible member is in an untwisted state.

2. The access port as recited in claim 1, wherein the first frame portion has a first end wall and first and second side walls extending from the first end wall, at least one of the first or second side walls having a receiving opening formed therein, and the second frame portion has a second end wall and third and fourth side walls extending from the second end wall, at least one of the third or fourth side walls terminating in a substantially linear portion insertable into the receiving opening.

3. The access port as recited in claim 2, wherein each of the first and second side walls terminates in a receiving opening and each of the third and fourth side walls terminates in a substantially linear portion insertable into the respective receiving openings of the first and second side walls.

4. The access port as recited in claim 3, wherein each of the first and second side walls includes a tapered portion.

5. The access port as recited in claim 1, wherein the outer frame includes a flexible member mounting surface on an underside thereof and the inner member includes a flexible member mounting surface.

6. The access port as recited in claim 1, wherein the inner member includes a flange substantially surrounding the second access opening.

7. The access port as recited in claim 1, wherein at least one of the outer frame or the inner member is substantially rectangular in configuration.

8. The access port as recited in claim 1, wherein the flexible member has a funnel shape narrowing in a direction toward the inner member.

9. The access port as recited in claim 1, wherein the inner member includes at least one tab configured for grasping by a tool to reconfigure the inner member for removal.

10. The access port as recited in claim 1, wherein movement of the at least one of the first or second frame portions to increase the length of the outer frame stretches the flexible member in a direction away from longitudinal edges of an elongated access incision in the patient.

11. The access port as recited in claim 1, wherein the first length of the outer frame is greater than the second length of the inner member and the first width of the outer frame is greater than the second width of the inner member.

12. The access port as recited in claim 11, wherein the second length of the inner member does not exceed the first width of the outer frame.

13. The access port as recited in claim 12, wherein the second length of the inner member is substantially equal to the first width of the outer frame.

14. The access port as recited in claim 1, wherein the inner member is transitionable between a natural state and a deformed state, the inner member having the non-circular configuration in the natural state.

15. A surgical access port for accessing a cavity of a patient comprising:
   an outer frame having first and second frame portions, at least one of the first or second frame portions movable with respect to the other one of the first or second frame portions, the outer frame having a first length along a first major axis thereof, wherein movement of the at least one of the first or second frame portions away from the other one of the first or second frame portions increases the length of the outer frame to a third length greater than the first length;
   an inner member having an access opening, the inner member having a non-circular configuration, the inner member having a second length along a second major axis thereof, a second width along a second minor axis thereof, and a lip adjacent the access opening, the lip extending proximally toward the outer frame, the entire lip positioned inwardly of an outer edge of the inner member, the second length being greater than the second width; and
   a flexible member extending between the outer frame and the inner member, the flexible member movable by movement of the at least one of the first or second frame portions, wherein the second major axis of the inner member is transverse to the first major axis of the outer frame when the flexible member is in an untwisted state.

16. The access port as recited in claim 15, wherein the outer frame includes a first width, the first length being greater than the first width.

17. The access port as recited in claim 15, wherein the access opening has a width and a length greater than the width, and the lip extends substantially around a perimeter of the access opening.

* * * * *